United States Patent [19]

Lehto

[11] Patent Number: 5,080,494

[45] Date of Patent: Jan. 14, 1992

[54] METHOD AND APPARATUS FOR MEASUREMENT OF DEWPOINT OF GASES

[75] Inventor: Ari Lehto, Helsinki, Finland

[73] Assignee: Vaisala OY, Helsinki, Finland

[21] Appl. No.: 701,341

[22] Filed: May 9, 1991

Related U.S. Application Data

[63] Continuation of Ser. No. 386,124, Jul. 28, 1989, abandoned.

[30] Foreign Application Priority Data

Aug. 3, 1988 [FI] Finland .................................. 883637

[51] Int. Cl.⁵ ...................... G01N 25/66; G01N 25/70
[52] U.S. Cl. .......................................... 374/17; 374/19
[58] Field of Search ..................... 374/17, 18, 19, 20, 374/27, 28

[56] References Cited

U.S. PATENT DOCUMENTS

| | | | |
|---|---|---|---|
| 2,654,242 | 10/1953 | Fallgatter et al. | 374/17 |
| 3,173,610 | 3/1965 | Feibush et al. | 374/28 |
| 3,540,826 | 11/1970 | Bisberg | 374/17 |
| 3,874,220 | 4/1975 | Sheldon | 374/18 |
| 4,083,249 | 4/1978 | Gerber | 374/20 |
| 4,179,917 | 12/1979 | Sheldon et al. | 374/18 |
| 4,377,001 | 3/1983 | Takeda et al. | 374/17 |
| 4,799,235 | 1/1989 | Bannell et al. | 374/18 |

FOREIGN PATENT DOCUMENTS

0813209  3/1981  U.S.S.R. .................. 374/17

*Primary Examiner*—William A. Cuchlinski, Jr.
*Assistant Examiner*—Diego F. F. Gutierrez
*Attorney, Agent, or Firm*—Birch, Stewart, Kolasch & Birch

[57] ABSTRACT

A method and an apparatus for measuring dewpoint of different kinds of gases is based upon cooling the measured gas by mixing it with a cold gas down to the dewpoint and then detecting the generated mist by optical sensors. The cooling gas is routed to a measurement area (7) from outside the process and the cooling gas is brought to an appropriate temperature below the dewpoint of the measured gas before being conducted to the measurement area (7) where it is mixed with the measured gas. Mist generated during the cooling of the measured gas is detected by illuminating the measurement area (7) by a light emitting source (8) and measuring the light (2) scattered from the mist or light (3) penetrating through the mist with the help of a photodetector (9).

2 Claims, 3 Drawing Sheets

METHOD AND APPARATUS FOR MEASUREMENT OF DEWPOINT OF GASES

This application is a continuation of application Ser. No. 07/386,124 filed on July 28, 1989, now abandoned.

BACKGROUND OF THE INVENTION

The present invention relates to a method for the measurement of dewpoint of gases in which method the measured gas is cooled with the help of cold gas down to the dewpoint, and the generated mist is detected optically.

The invention also concerns an apparatus applicable for the implementation of the method.

Significant energy savings are possible in industrial processes by means of optimizing the conditions of the drying process. Dewpoint is one of major parameters associated with these processes. The measured dewpoint can be, e.g., the dewpoint of exhaust air from the dryer hood of a paper machine or the acid dewpoint of flue gases from a coal-fired power plant.

Several different methods are currently available for the measurement of dewpoint. The most common type of optical dewpoint measurement devices might be the "chilled-mirror" detector, in which humidity precipitating on a cold, mirror-polished plane will cause a change in the optical measurement signal. This device is extremely accurate in clean conditions but noncompatible with the actual contaminating conditions in process use. The direct measurement of dewpoint can also employ change of capacitance or resistance, but these methods are hampered by the same contamination problems as the chilled mirror.

The indirect optical measurement of dewpoint is based on absorption in the UV or IR bands of the vapour. The measurement gives the absolute moisture content, from which the dewpoint can then be computed. Contamination and high process temperatures make the continuous use of these kinds of methods unreliable in industrial processes. Other methods available for absolute humidity measurement are based on the use of microwave and acoustic emissions. The former method is based on microwave absorption and/or change in the dielectric factor of air caused by water vapour. The microwave method is costly to implement while otherwise a feasible solution. A transducer based on acoustic emission is hampered by its large dimensions and the high costs of correlation techniques required.

Dewpoint can also be determined with the help of relative humidity measuring equipment if sensor temperature is known. Dewpoint then becomes a computational variable. Consequently, direct measurement of dewpoint gives a better alternative, since an indirect measurement device can output a computational dewpoint even if the transducer is defective.

SUMMARY OF THE INVENTION

A humidity sensor in accordance with this invention is superior to prior art sensors in dewpoint measurement in industrial processes.

The invention is based on cooling the process gas down to its dewpoint with the help of a cold gas and then determining the dewpoint by means of light scattered from or penetrated through the developed mist.

More specifically, the method in accordance with the invention is characterized in that: the cooling gas is routed to a measurement area from outside the process; prior to its conduction to the measurement area, the cooling gas is brought to the appropriate temperature below the dewpoint of the measured gas, and the mist generated during the cooling of the measured gas is detected by illuminating the measurement area by a light source and measuring the light scattered from the mist and/or the light penetrated through the mist with the help of a photodetector.

Furthermore, the apparatus in accordance with the invention characterized in that the apparatus is provided with a heater/cooler element, with which the cooling gas can be brought to a proper temperature below the dewpoint of the measured gas, and the measurement area is situated at the end of a core pipe, where a second side pipe is also routed in order to mix the measured gas with the cooling gas.

The invention provides outstanding benefits.

The apparatus in accordance with the invention is capable of measuring dewpoint in several different gases. In industrial processes, dewpoint to be determined could be, for instance, water vapour dewpoint or acid vapour dewpoint. The equipment can be fabricated from materials compatible with rugged operating environments, and air passing through the apparatus simultaneously provides for the cleaning of apparatus, which allows its installation into the most contaminating process conditions. The optical part of the apparatus can be manufactured from standard components. A suitable light source is the so-called superluminescent LED while the detector can be of a standard type photodiode. Temperature within the mist generation area can be measured using one or several thermocouples or other suitable sensors.

The operating principle of the invention and the construction of the apparatus in accordance with the invention is next examined in detail.

BRIEF DESCRIPTION OF THE DRAWINGS

The invention will now be described by way of example in more detail with reference to the accompanying drawings in which.

DETAILED DESCRIPTION OF THE INVENTION

Figure 1:
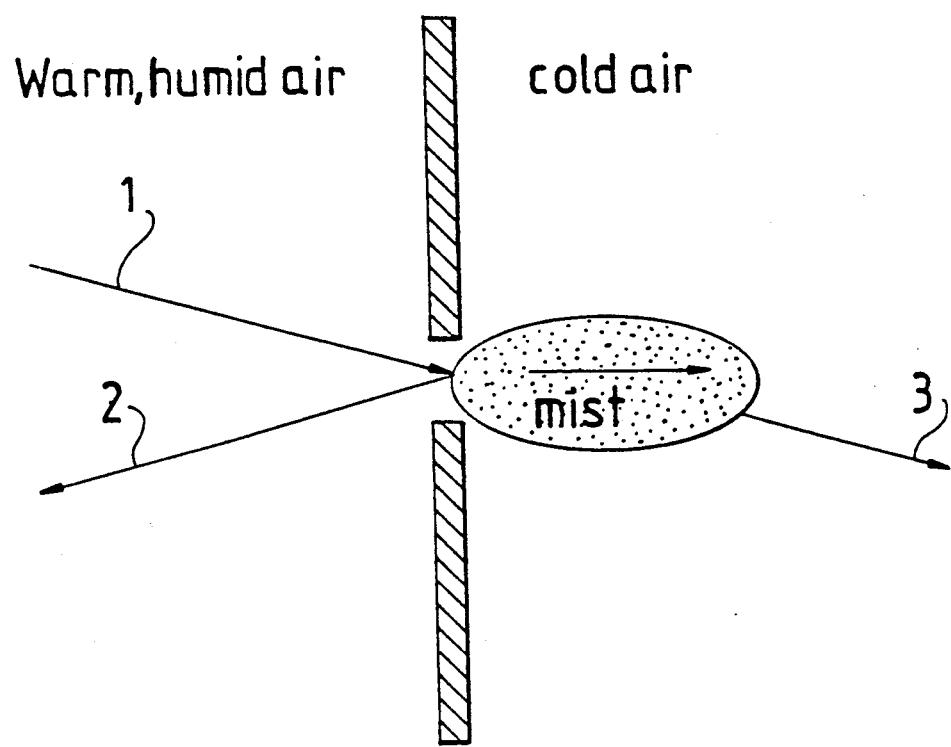
FIG. 1 shows the method in accordance with the invention and the operating principle of the apparatus.

The operating principle of the apparatus ±n accordance with the invention is illustrated in FIG. 1. The hot process gas is cooled by mixing it with cold air, whereby mist droplets are formed. The mist generation area is illuminated by light 1 with high intensity so that light 2 scattered from the mist or, alternatively, light 3 penetrating the mist can be detected. With an increase in the concentration of mist droplets, the intensity of the scattered light 2 is increased, while the intensity of the penetrated light 3 is decreased.

Figure 2:
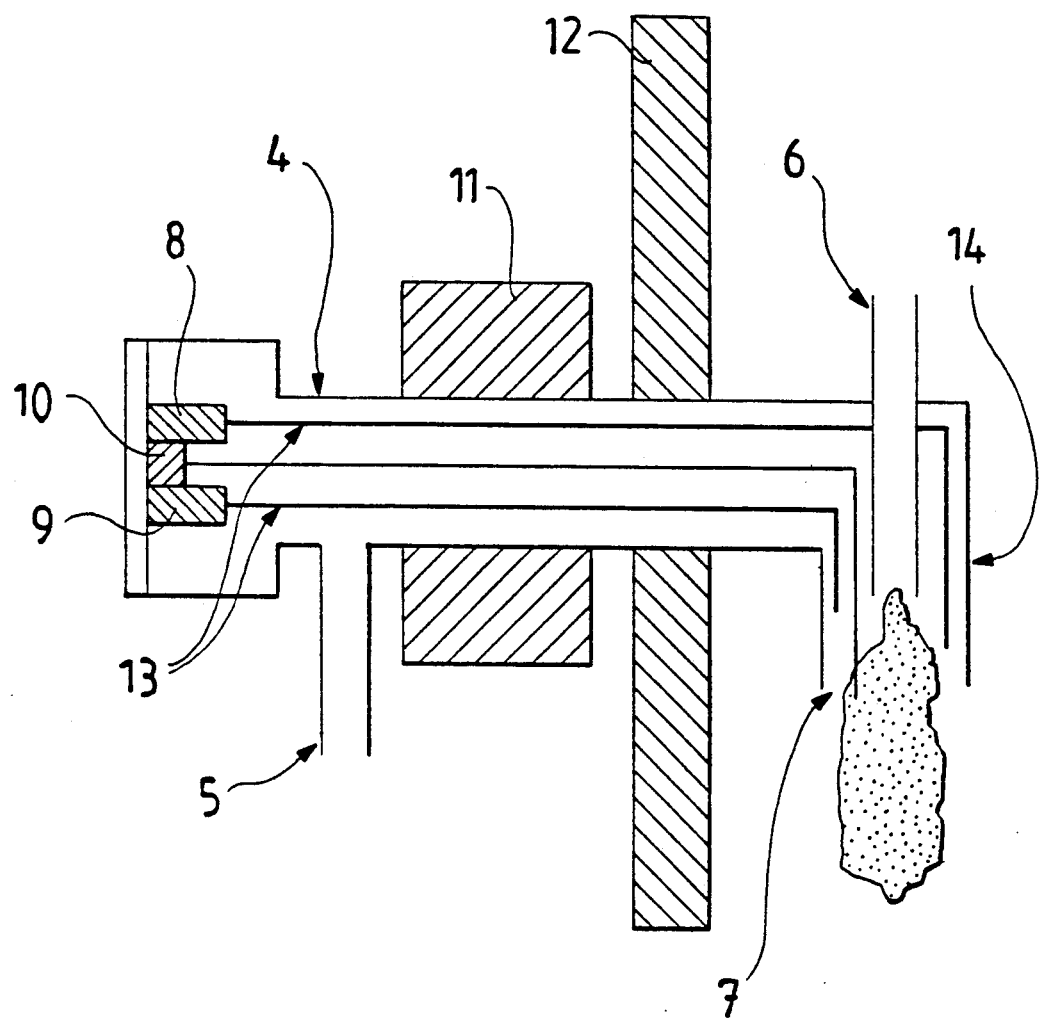
FIG. 2 shows the schematic structure of the apparatus for measuring scattered light in accordance with the invention.
Figure 3:
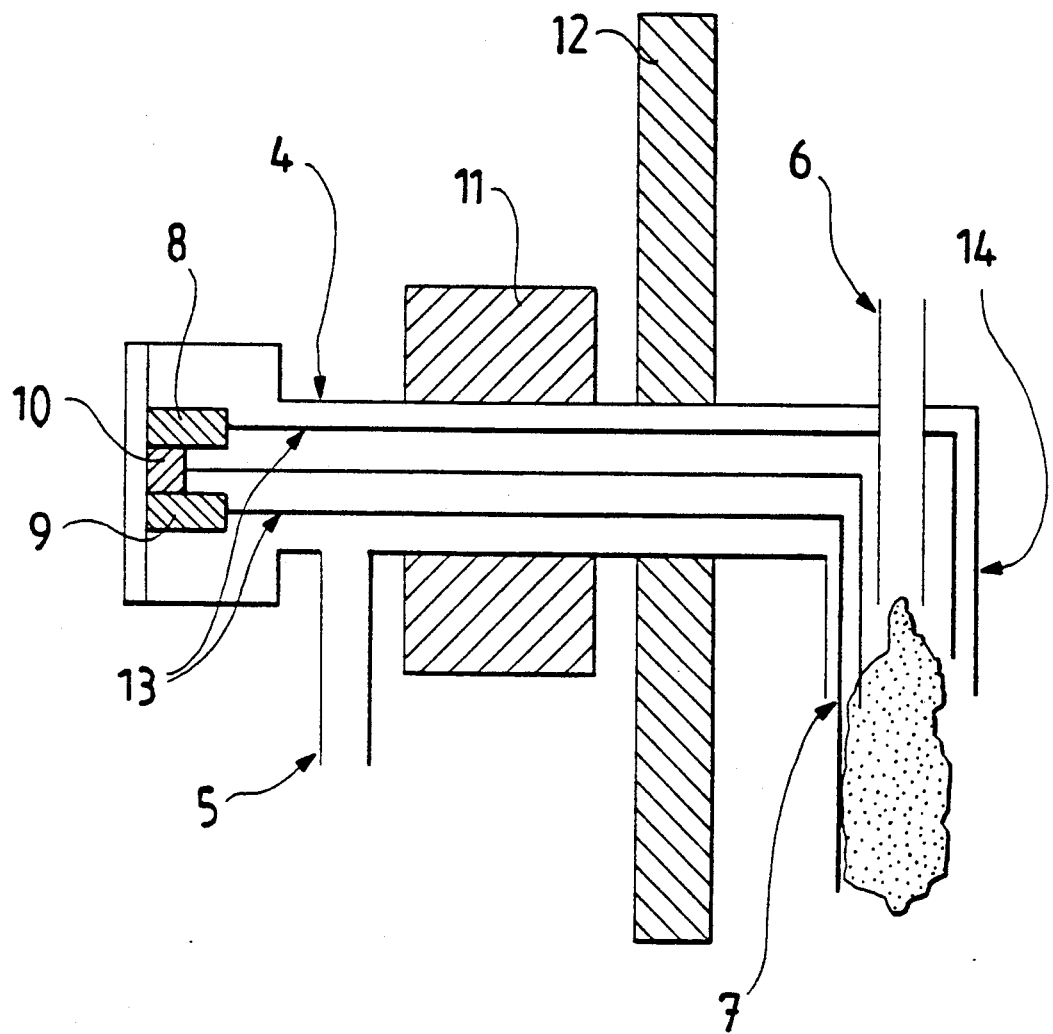
FIG. 3 shows the schematic structure of the apparatus for measuring penetrated light in accordance with the invention.

FIGS. 2 and 3 illustrate the operating principle and structure of the apparatus. The core pipe 4 of the apparatus is routed through a separating wall 12 to the process to be measured. Clean air is conducted via a side pipe 5 into the core pipe 4. Air flow within the core pipe 4 is maintained approximately constant. The hot and humid process gas is routed into the equipment via a second side pipe 6. By means of a heater/cooler element 11, the clean air is cooled or heated as necessary to a proper temperature, which is lower than the dewpoint temperature in the process gas. Process gas entering from pipe 6 is mixed with the cold gas within the measurement area 7, whereby mist droplets are formed at this point. The area 7 is illuminated by means of a light emitting diode (LED) 8 and light scattered from the mist droplets or penetrating the mist is detected by means of a photodetector 9. Light is transmitted from the diode 8 to the area 7 and then from the area 7 to the detector 9 with the help of optical fibers 13. Upon detection by the photodetector 9 of mist generated at the dewpoint of the process gas, the temperature of dewpoint at the measurement area 7 is measured with the help of one or several thermocouples 10 or other temperature sensor having a low thermal mass. In FIG. 2 the optical fiber 13 leading to photodetector 9 extends into the mist in order to measure scattered light, while in FIG. 3 the optical fiber 13 leading to photodetector 9 extends beyond the mist in order to measure penetrated light.

The light-emitting diode 8, photodetector 9, heater/cooler element 11 and side pipe 5 are located outside the actual process. The light emitting diode 8 and the photodetector 9 are placed within the core pipe 4. The side pipe 5 is attached to the core pipe 4 next to the light emitting diode 8 and photodetector 9. The heater/cooler element 11 is adapted around the core pipe 4, after the side pipe 5 and before the intermediate wall 12. Into the actual process environment is inserted only a section of the core pipe 4 including its head 14, which comprises the measurement area 7, side pipe 6 as well as optical fibers 13 and a part of thermocouple(s) 10. The thermocouple(s) 10 and optical fibers 13 are routed through the intermediate wall 12 into the process environment within the core pipe 4 The end 14 of the core pipe is aligned perpendicular to the actual core pipe 4 and parallel with the side pipe 6.

Alternative constructional embodiments, different from the above described embodiment are possible within the scope of invention. Thus, the light emitting diode 8, photodetector 9 and connection of thermocouple(s) can be arranged into a separate unit outside the core pipe 4.

What is claimed is:

1. A method for measuring the dewpoint in different gases, in which method a measured gas is cooled with the help of cold gas down to the dewpoint, and a generated mist is detected optically, comprising the steps of:
   (1) providing a cooling gas;
   (2) bringing said cooling gas to an appropriate temperature below the dewpoint of a measured gas;
   (3) conveying said cooling gas to a measurement area;
   (4) conveying said measured gas into said measurement area for mixing with said cooling gas;
   (5) determining the presence of said mist by illuminating the measurement area with a light source and detecting the light scattered by the mist with the help of a photodetector; and
   (6) measuring the dewpoint temperature of said measured gas by a temperature sensor upon detecting an increase in the light scattered by the mist.

2. A method for measuring the dewpoint in different gases, in which method a measured gas is cooled with the help of cold gas down to the dewpoint, and a generated mist is detected optically comprising the steps of:
   (1) providing a cooling gas;
   (2) bringing said cooling gas to an appropriate temperature below the dewpoint of a measured gas;
   (3) conveying said cooling gas to a measurement area;
   (4) conveying said measured gas into said measurement area for mixing with said cooling gas to generate a mist;
   (5) determining the presence of said mist by illuminating the measurement area with a light source and detecting the light penetrated through the mist with the help of a photodetector; and
   (6) measuring the dewpoint temperature of said measured gas by a temperature sensor upon detecting a decrease in the light penetrated through the mist.

* * * * *